United States Patent [19]

Armbruster et al.

[11] Patent Number: 5,914,103
[45] Date of Patent: Jun. 22, 1999

[54] SINGLE APPLICATION SHAVING LOTION FOR USE PRIOR TO AND AFTER SHAVING WITH ELECTRIC RAZOR

[76] Inventors: Joseph M. Armbruster; Sue B. Armbruster, both of 2700 NE. 47 St., Lighthouse Point, Fla. 33064

[21] Appl. No.: 08/646,108

[22] Filed: May 7, 1996

[51] Int. Cl.[6] .............................. A61K 7/06; A61K 7/15
[52] U.S. Cl. ...................... 424/73; 424/70.9; 424/70.11; 424/70.13; 424/74; 424/401; 514/844
[58] Field of Search ........................... 424/73, 401, 70.9, 424/70.11, 70.13, 74, 59; 514/844

[56] References Cited

U.S. PATENT DOCUMENTS

| | | | |
|---|---|---|---|
| 4,482,537 | 11/1984 | El-Menshawy et al. | 424/59 |
| 4,994,265 | 2/1991 | White | 424/73 |

*Primary Examiner*—Thurman K. Page
*Assistant Examiner*—James M. Spear
*Attorney, Agent, or Firm*—Jacobson, Price, Holman & Stern, PLLC

[57] ABSTRACT

A shaving lotion used when shaving with an electric razor. The shaving lotion includes a combination of lubricants, vitamins, aloe vera, moisturizers, sunscreen with or without sunless tanning and/or fragrance and other constituents to act as a skin enhancing and protecting product which also serves to reduce the appearance of fine lines in the skin surface. The shaving lotion is applied by utilizing a roller ball applicator prior to shaving with an electric razor and has the ability to orient the whiskers or hair vertically or perpendicular to the surface being shaved so that the whole hair shaft can effectively be directed through holes found in the foil shaver or through the grill openings found in a rotary shaver to cut the hair close to the skin surface. After shaving, the light residue of shaving lotion that remains on the skin surface is briskly rubbed into the skin surface to provide skin enhancement and protection.

1 Claim, No Drawings

SINGLE APPLICATION SHAVING LOTION FOR USE PRIOR TO AND AFTER SHAVING WITH ELECTRIC RAZOR

BACKGROUND OF THE INVENTION

1. Field of the Invention

The present invention generally relates to a shaving lotion used when shaving with an electric razor. The shaving lotion includes a combination of lubricants, vitamins, aloe vera, moisturizers, sunscreen with or without sunless tanning and/or fragrance and other constituents which act as a skin enhancing and protecting product which also serves to reduce the appearance of fine lines in the skin surface. The shaving lotion is applied by utilizing a roller ball applicator prior to shaving with an electric razor and has the ability to orient the whiskers or hair vertically or perpendicular to the surface being shaved so that the whole hair shaft can effectively be directed through holes found in the foil shaver or through the grill openings found in a rotary shaver to cut the hair close to the skin surface. After shaving, the light residue of shaving lotion that remains on the skin surface is briskly rubbed into the skin surface to provide skin enhancement and protection.

2. Description of the Prior Art

Individuals who commence to use electric shavers frequently experience razor rash caused by the razor head dragging across dry skin. Manufacturers of electric shavers frequently include statements reassuring purchasers that after shaving for a time period, the skin will become acclimated to the use of electric shavers and that the user will no longer experience razor rash.

In recent years, electric shaver manufacturers have produced battery powered shavers that are advertised for use in the shower with either running water or shaving cream providing lubrication. The purpose of shaving in the shower is to add a degree of lubrication to the skin surface that is otherwise not experienced when dry shaving. When shaving in the shower, the whiskers or hair becomes wet and limp and lays over against the skins surface which causes a problem since both foil type or rotary type shavers require that the hair must be directed through the holes in the foil or through the slots in the rotary grill for cutting the hair by the movable blade. This results in the user of the electric shaver using many strokes trying to coax or direct the hairs through these opening so that they can be cut. Even so, wet hair will not "stand up". Therefore, even if the hair is cut, it will usually be cut adjacent the outer end on the first stroke thereby requiring many more strokes until the hair is cut as close to the skin as possible.

Experience has shown that wet shaving with an electric razor causes as much or more razor rash as dry shaving. Also, when wet shaving, it is difficult to feel uncut hair or whiskers since they are laid over against or next to the skin surface. In addition, wet shaving in the shower negates one of the main features of electric shaving that is, it defeats mobility in which a user can shave anywhere by dry shaving. Thus, wet electric shaving becomes an alternate to wet blade shaving. Further, if the user wears glasses, it is not practical to wear glasses in the shower environment which reduces the ability of a person to see their face or skin surface which is essential when properly shaving with any degree of accuracy especially when shaving at the lower edge of side burns or adjacent a mustache or the like.

Many preshaving lotions are on the market and all of these must be thoroughly washed off after shaving thus requiring a source of water which defeats mobility. Also, there is a large variety of post shaving lotions on the market to soothe the ravished skin after shaving. These products create a time consuming, ineffective and costly two step operation.

SUMMARY OF THE INVENTION

An object of the present invention is to provide a shaving lotion for use when shaving with an electric razor applied to the skin surface prior to shaving with residual lotion remaining on the skin surface after completion of shaving being rubbed into the skin surface to provide skin enhancement and protection when shaving with an electric razor.

Another object of the invention is to provide a shaving lotion for application to the skin surface when shaving with an electric razor which includes a combination of lubricants, vitamins, aloe vera, moisturizers, sunscreen with or without sunless tanning and/or fragrance and other constituents to act as a skin enhancing and protecting product which also serves to reduce the appearance of fine lines in the skin surface.

A further object of the invention is to provide a shaving lotion for use when shaving with electric razors which has the ability to coax the hair or whiskers vertically or perpendicularly to the skin surface so that the entire hair shaft is effectively directed through the holes found in the foil shaver or through the grill openings found in a rotary shaver in order to cut the hair close to the skin surface.

Still another object of the invention is to provide a shaving lotion in accordance with the preceding objects which negates the use of water or after shave product with the shaving lotion of this invention reducing razor burn and rash and does not ravish the skin even if the user makes repetitious strokes thereby enabling the user to obtain an extremely close, rash free shave. By applying the lotion to the entire facial area, the user obtains post shaving skin enhancement and protection not found in any marketed electric shaving preshaving or post shaving products.

A still further object of the invention is to provide a shaving lotion for use when shaving with an electric razor in which the formulation has a viscosity and surface tension which renders it near impossible to apply to the skin surface when the lotion is merely poured into the palm of a hand to apply to the face or other skin surface by surface contact inasmuch as the lotion rolls off the open hand when the hand is tilted or rotated in a manner similar to the manner in which mercury rolls from the palm when the hand is tilted or rotated. This application characteristic of the lotion is solved by utilizing a roller ball applicator or dispenser such as those that are commercially available for use in applying liquid deodorant to under arm areas or other body skin surfaces to apply the shaving lotion of the invention.

The above together with other objects and advantages which will become subsequently apparent reside in the details of the shaving lotion as more fully hereinafter described and claimed.

DESCRIPTION OF THE PREFERRED EMBODIMENTS

The shaving lotion of the present invention is used when shaving with an electric razor without the application of water prior to shaving and without the application of water subsequent to shaving. The shaving lotion is applied to the skin surface by the use of a roller ball applicator, such as one having a three fluid ounce capacity, which is used to apply the shaving lotion prior to shaving. The lotion should be applied to substantially the entire surface to be shaved even though it is not necessary to cover the surface area in totality since the lotion can be distributed over the skin surface by using an open hand after the lotion has been applied by the applicator with the lotion being rubbed in until it virtually disappears inasmuch as it dries fast.

When applied prior to shaving, the shaving lotion has the ability to orient or coax the hair or whiskers vertically or in perpendicular relation to the skin surface in order that the whole hair shaft can be effectively directed through the holes found in the foil type electric shaver or through the grill openings found in the rotary type electric shaver thereby enabling the hair or whiskers to be cut close to the skin surface. The shaving lotion will thwart or reduce razor burn and rash even if the user makes repetitious strokes. The user of the shaving lotion will experience an extremely close, rash free shave and the skin surface has been provided with post shaving skin enhancement and protection not found in any other marketed electric shaving lotions. The skin enhancement and protection is obtained by the shaving lotion by briskly rubbing into the skin surface any residue shaving lotion remaining on the skin surface. The use of the shaving lotion of this invention negates the use of any water or other preshave or after shave product. The shaving lotion provides the same skin lubrication, enhancement and protection properties contained in our Gel Cream used in our waterless shaving systems disclosed in copending application U.S. Ser. No. 08/550,002 filed Oct. 30, 1995. The shaving lotion of this invention allows men and women to electric shave rash free and closer than previously capable thereby expanding the use of electric shavers.

The electric shaving lotion formula of this invention is as follows:

Electric Shaving Lotion Formula
With Vitamins A, E and C, Aloe Vera, Allantoin and Natural SPF2

| Material | % w/w |
|---|---|
| Water | 40–50% |
| SDA Alcohol 38 or 41 | 20–40% |
| Camphor | .1–2.5% |
| Dimethyl Glucose | .35–3% |
| Isopropyl Palmatate | .1–5% |
| Isopropyl Myristate | .1–5% |
| Vitamin E Linoleate | .5–3% |
| Vitamin A Palmatate | .25–3% |
| Ascorbic Acid | .1–10% |
| Titanium Dioxide | .1–3% |
| Zinc Oxide | .05–3% |
| Aloe Vera Gel | .5–10% |
| Fragrance | .05–.5% |
| Carbopol 940 | .1–2% |
| Triethanolamide | .05–2% |
| Carrageenan | .05–3% |
| Glycerin | 1–5% |
| Methyl Paraben | .05–.3% |
| Propyl Paraben | .05–.25% |
| Allantoin | .1–2% |
| Q.S. to | 100% |

In using the shaving lotion a three fluid ounce roller ball applicator or dispenser will provide sufficient lotion for approximately 100 shaves. However, smaller travel size applicators may be used if desired. Due to the small dimensional characteristics of the roller applicator, it is entirely portable thereby allowing electric shaving without the necessity of water thus maintaining the mobility benefits of using an electric razor as compared to existing electric shaving lotions which require a source of water in order to "wash off" after shaving. In distinction, the shaving lotion of this invention enables any residue that may remain on the skin surface to be briskly rubbed into the skin of the face and/or the arms thereby providing skin enhancement and protection.

The formula may also include increased sunscreen for UV protection factor from SPF 2 up to SPF 15 to help prevent UV related skin cancer. The formula also includes a sunless tanning ingredient and a variety of fragrances that may be dictated by market conditions.

The foregoing is considered as illustrative only of the principles of the invention. Further, since numerous modifications and changes will readily occur to those skilled in the art, it is not desired to limit the invention to the exact formulation as described, and, accordingly, all suitable modifications and equivalents may be resorted to, falling within the scope of the invention.

What is claimed as new is as follows:

1. A shaving lotion for use when shaving with an electric razor comprising a lotion applied to the skin surface to be shaved prior to electric shaving without the use of water with residual lotion remaining on the skin surface being briskly rubbed into the skin surface after electric shaving for enhancing and protecting the skin surface, said lotion including ingredients as follows:

Electric Shaving Lotion Formula
With Vitamins A, E and C, Aloe Vera, Allantoin and Natural SPF2

| Material | % w/w |
|---|---|
| Water | 40–50% |
| SDA Alcohol 38 or 41 | 20–40% |
| Camphor | .1–2.5% |
| Dimethyl Glucose | .35–3% |
| Isopropyl Palmatate | .1–5% |
| Isopropyl Myristate | .1–5% |
| Vitamin E Linoleate | .5–3% |
| Vitamin A Palmatate | .25–3% |
| Ascorbic Acid | .1–10% |
| Titanium Dioxide | .1–3% |
| Zinc Oxide | .05–3% |
| Aloe Vera Gel | .5–10% |
| Fragrance | .05–.5% |
| Carbopol 940 | .1–2% |
| Triethanolamide | .05–2% |
| Carrageenan | .05–3% |
| Glycerin | 1–5% |
| Methyl Paraben | .05–.3% |
| Propyl Paraben | .05–.25% |
| Allantoin | .1–2% |
| Q.S. to | 100% |

\* \* \* \* \*